United States Patent
Smith

(10) Patent No.: US 6,737,524 B2
(45) Date of Patent: May 18, 2004

(54) ACTIVATED POLYETHYLENE GLYCOL COMPOUNDS

(75) Inventor: Paul K. Smith, 6807 Kinnikinnick Dr., Roscoe, IL (US) 61073

(73) Assignee: Paul K. Smith, Roscoe, IL (US)

( * ) Notice: Subject to any disclaimer, the term of this patent is extended or adjusted under 35 U.S.C. 154(b) by 93 days.

(21) Appl. No.: 10/105,644

(22) Filed: Mar. 25, 2002

(65) Prior Publication Data

US 2003/0187248 A1 Oct. 2, 2003

(51) Int. Cl.$^7$ .......................... C07C 331/28; C08B 3/00
(52) U.S. Cl. .................. 536/32; 536/48; 536/51; 536/53; 552/6; 558/17
(58) Field of Search ................. 558/17; 536/51, 536/32, 48, 53, 30, 45, 54; 552/6

(56) References Cited

U.S. PATENT DOCUMENTS

| | | |
|---|---|---|
| 4,220,717 A | 9/1980 | Kuo |
| 4,356,170 A | 10/1982 | Jennings et al. |
| 5,349,052 A | 9/1994 | Delgado et al. |
| 5,585,468 A * | 12/1996 | Coughlin et al. ............. 534/14 |
| 5,585,484 A | 12/1996 | Acharya et al. |
| 5,750,725 A | 5/1998 | Acharya et al. |
| 5,880,255 A | 3/1999 | Delgado et al. |
| 6,017,943 A | 1/2000 | Acharya et al. |
| 6,312,916 B1 | 11/2001 | Kopetzki et al. |

FOREIGN PATENT DOCUMENTS

| | | |
|---|---|---|
| EP | 0 126 043 A1 | 11/1984 |
| EP | 0126 043 B1 | 11/1984 |
| EP | 0157 899 A2 | 10/1985 |
| EP | 0 157 899 B1 | 10/1986 |

OTHER PUBLICATIONS

Kricheldorf et al. Chemical Abstracts, 95:25583, 1981.*
Viswanathan et al., Indian Journal of Chemistry, 20B, 308–310, 1981.*
Jerry E. Squires, *"Artificial Blood", Science*, 295:1002, 1004–1005 (Feb. 8, 2002).
J. Milton Harris, ed., *Poly(ethylene Glycol) Chemistry: Biotechnical and Biomedical Applications: Topics in Applied Chemistry*, Plenum Press (New York: 1992), pp. 1–379.
J. Milton Harris and Samuel Zalipsky, eds., *Poly(ethylene Glycol) Chemistry and Biological Applications: ACS Symposium Series 680*, American Chemical Society Publishing (Washington, D.C.: 1977), p. 1–341.
Shearwater Corporation, *Catalog 2001: Polyethylene Glycol and Derivatives for Biomedical Applications*, Huntsville, AL 35801, (pp. 1–17).
Susan Budavari, et al., eds., *Merck Index, 11$^{th}$ Ed.*, Merck & Co., Inc. (Rahway, N.J.: 1989), p. 7275, Compound No. 7268.
Porro et al., *"Specific Antibodies to Diphtheria Toxin and Type 6A Pneumococcal Capsular Polysaccharide Induced By A Model of Semi–Synthetic Glycoconjugate Antigen "* (1985) *Mol. Immunol.*,22:907–919.
Anderson et al., *"Vaccines Consisting of Periodate–Cleaved Oligosaccharides from the Capsule of Haemophilus Influenze Type b Coupled to a Protein Carrier: Structural and Temporal Requirements for Priming in the Human Infant,"* (1986) *J. Immunol.*, 137:1181–1186.
Witte et al., *"Enzymatic Glycoprotein Synthesis: Preparation of Ribonuclease Glycoforms via Enzymatic Glycopeptide Condensation and Glycosylation,"* (1997) *J. Am. Chem. Soc.*, 119:2114–2118.
Michael E. Annunziato, et al., *"p–Maleimidophenyl Isocyanate: A Novel Heterobifunctional Linker for Hydroxyl to Thiol Coupling,"* Bioconjugate Chem., 4:212–218 (1993).
Aldrich, *Aldrich: Catalog Handbook of Fine Chemicals*, (1998–1999), p. 83, Product No. 18,627–9.
Belur N. Manjula, et al., *"Cys–93–ββ Succinimidophenyl Polyethylene Glycol 2600 Hemoglobin A: (Intramolecular Cross–Bridging of Hemoglobin Outside the Central Cavity,"* J. Biol. Chem., 275(8):5527–5534 (2000).
Polymasc Pharmaceuticals, PLC, "Attachment of Polyethylene Glycol (PEG)," taken from www.polymasc.com/PEG/htm (Feb. 8, 2000).
Polymasc Pharmaceuticals, PLC, "Biological Optimisation and Its Importance," taken from www.polymasc.com/PEGi-i.htm (Feb. 8, 2000).

* cited by examiner

*Primary Examiner*—Fiona T. Powers
(74) *Attorney, Agent, or Firm*—Welsh & Katz, Ltd.

(57) ABSTRACT

Novel arylisothiocyanate compounds are described that are useful for activating alcohol-containing macromomolecules, for example polyethyleneglycols and cellulose, for covalent linkage to amino-groups of biomolecules, for example polypeptides such as antibodies, enzymes, and proteins.

8 Claims, No Drawings

ACTIVATED POLYETHYLENE GLYCOL COMPOUNDS

TECHNICAL FIELD

The present invention relates to a novel compound and method for preparation of polyethylene glycol (PEG) adducts of biomolecules, and particularly to PEG adducts of proteins and peptides.

BACKGROUND OF THE INVENTION

Attachment of large macromolecules such as polyethylene glycol (PEG) to biomolecules such as proteins or peptides via chemical attachment is desired for modification of the properties of the proteins or peptides. Linking to PEG is referred to in the art as "pegylation". Biomolecules circulating in the blood outside of a cell are subject to clearance, and can move through blood vessel walls (extravascularization). Attachment of relatively small biomolecules to large macromolecules can reduce extravascularization, and can enhance the in-vivo circulation half-life of the biomolecule.

Increasing half-life of the biomolecule in circulation is particularly important when the biomolecule is intended for therapeutic use. Pegylation of certain biomolecules reduces kidney clearance and spurious enzymatic degradation and immune system recognition. In "Artificial Blood", *Science*, 295:1002, 1004–1005 (Feb. 8, 2002), Jerry E. Squires cites literature reports that conjugation of hemoglobin to macromolecules such as dextran, polyethylene glycol or polyoxyethylene retards the rate at which cell-free hemoglobin is cleared from blood circulation, extending intravascular dwell time up to 48 hours. The alteration of the effective solution volume of the hemoglobin through linkage to a macromolecule alters the colligative properties of cell-free hemoglobin, including osmotic pressure that appears to have a significant effect on blood pressure.

Polyethylene glycol is approved by the U.S. Food and Drug Administration for internal and topical use due to its low toxicity. Additional utilities and features of PEG-biomolecule conjugates are described in *Polyethylene Glycol Chemistry: Biotechnical and Biomedical Applications*, J. M. Harris, ed. Plenum, NY, 1992 and *Polyethylene Glycol Chemistry and Biological Applications*, J. M. Harris and S. Zalipsky, eds., ACS, Washington, 1997.

A requisite for preparation of polyethylene glycol conjugates of biomolecules is a suitably activated PEG molecule that under proper conditions reacts with a target biomolecule in an efficient, predictable manner such that the native activity of the target biomolecule is not adversely affected to a significant degree. For sensitive target biomolecules such as proteins and peptides, reactions to form PEG conjugates are best conducted in aqueous, buffered systems in order to avoid denaturation and concomitant loss of biological activity.

Most, if not all, activated polyethylene glycol compounds described in the patent and scientific literature and intended for conjugation to biomolecules such as proteins react with water in addition to the target biomolecule. See, for example, Scheme I below. Typically, the conundrum of derivatizing a target biomolecule in an aqueous medium with a water-sensitive; activated, polyethylene glycol reagent is partially solved by employing a large excess (5–10 fold) of reagent, while maintaining rigorous control of pH and temperature. An objective of any pegylation procedure is to produce pegylated biomolecules with stable, enhanced physiological properties in a predictable and reproducible manner on a meaningful, economical scale.

Scheme 1, below represents a reaction between an activated pegylation reagent of the art and a biomolecule reactant having acidic hydrogens (hydrido groups). The scheme shows the formation of hydrolysis product, pegylated biomolecule and protonated leaving group (HA). As illustrated in Scheme 1, activated pegylation reagents described in the current art often involve production of a leaving group (HA in Scheme 1 below) in addition to any hydrolyzed PEG reagent (shown as PEG-OH). The production of a leaving group presents an additional workup and purification problem during the isolation of the PEG-modified target molecule. The extent of the isolation/purification problem is influenced by the magnitude of the excess reagent employed in order to achieve the desired level of PEG modification which, in turn, is a function of hydrolysis rate of the reagent in water and the coupling rate onto a residue of the target molecule (typically —$NH_2$ or —SH).

Scheme 1

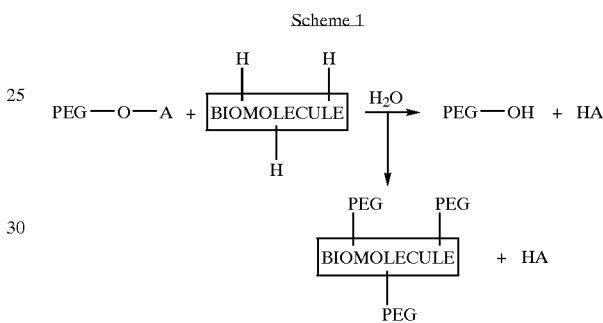

Typically, activated polyethylene glycol reagents described and used in the current art are acylating reagents directed toward primary amine residues (—$NH_2$) in the target biomolecule. A common type of PEG acylating reagent is the so-called "active ester" derivative of PEG. Active ester PEGs of the N-hydroxysuccinimide (NHS), hydroxybenztriazole (HBT), imidazole (IM) and p-nitrophenol (PNP) have been described and are commercially available. (See Shearwater Corporation, Catalog 2001, Huntsville, Ala. 35801, www.shearwatercorp.com).

Reagents of the type

where R=(O)C—$(CH_2)_y$ or $(CH_2)_y$ or (—O—), y=zero through 4, and

X=NHS, HBT, IM or PNP exhibit half-lives of hydrolysis of 1 minute (or less) to approximately 24 minutes at pH=8 and 25° C. Further, as half-life goes up, reactivity goes down. Recommended excesses of PEG acylating reagent vary from equal mass to 10-fold mass relative to target molecule (Shearwater Catalog 2001 p.12). Depending on the molecular weight of the target biomolecule, this recommended mass excess can be greater than a 100–1000 molar excess.

Incorporation of macromolecules such as PEG into biomolecules by using currently-available PEG acylating reagents is a demonstrably inefficient process. Problems associated with the acylating PEG reagents of the current art are exacerbated on a large scale. Variables affecting efficiency and reproducibility of pegylation procedures based on current art acylating reagents include: half-life ($t_{1/2}$) of hydrolysis, pH value, temperature, time, mixing rate, nature and toxicity of leaving group, ease of product purification from leaving groups and hydrolyzed reagent, as well as the rate and extent of reactivity of the reagent toward the target biomolecule.

The rapid hydrolysis rates of acylating PEG reagents employed by the standard art preclude practical application of multi-functional, crosslinking pegylation reagents of the following type, where A is a leaving group.

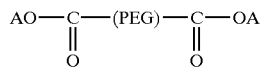

A multifunctional, activated PEG reagent as shown above is useful for establishing intramolecular cross-links within protein molecules for the purpose of mapping sub-unit geographies and for stabilization of protein configurations and activities. Rapid hydrolysis rates of standard art PEG reagents, used at large molar excess favor a preponderance of "one on hits", where one carboxyl end of the bifunctional molecule links to the target protein but the other end hydrolyzes to a carboxylic acid instead of also linking to the protein, and forming stabilizing cross-links.

In a significant advance, workers at the Albert Einstein College of Medicine of Yeshiva University N.Y., University of Iowa and BioAffinity Systems describe a novel approach for activating PEG for attachment to biomolecules that largely circumvents problems associated with hydrolytically unstable reagents. As disclosed in Acharya et al. U.S. Pat. No. 5,585,484, U.S. Pat. No. 5,750,725, U.S. Pat. No. 6,017,943, entitled "Hemoglobin Crosslinkers", and Belur N. Manjula, et al., *J. Biol. Chem.*, 275(8):5527–5534 (2000), a maleimide-activated PEG reagent is employed to form stable thioether bonds with an indigenous or added sulfhydryl moiety in the biomolecule. The maleimide function reacts rapidly with —SH groups without significant hydrolysis at pH 6.5–7.0 and without the production of a leaving group as is shown in the reaction below, wherein R—SH is a sulfhydryl-containing biomolecule.

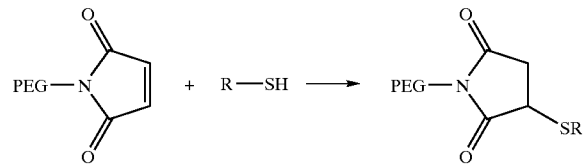

Biomolecules such as a protein having a paucity of —SH groups must first be reacted with a thiolating reagent such as 2-iminothiolane (or the like) to convert native —NH$_2$ groups from lysine into —SH groups. A practical drawback with the maleimide reagents is that they are difficult molecules to obtain synthetically.

The chemical formula of phenyl isothiocyanate, also known as isothiocyanatobenzene or isothiocyanic acid phenyl ester is shown below.

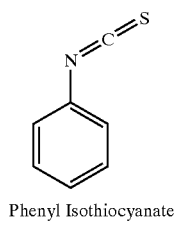

Phenyl Isothiocyanate

As noted in the *Merck Index*, 11$^{th}$ Ed., Susan Budavari, et al., eds., Merck & Co., Inc. (Rahway, N.J.: 1989), p. 7275, phenyl isothiocyanate is known to be used as a derivatizing agent for primary and secondary amines. Such derivatization of primary and secondary amines has typically been used for carrying out Edman degradation and amino acid analyses by HPLC.

This art does not teach the introduction of macromolecules such as polyethylene glycol by the use of a phenylisothiocyanate-containing molecule. Nor are there available any commercial sources of polyethylene glycols or other such macromolecules activated with phenylisothiocyanate. Furthermore, the precursors for obtaining such activated macromolecules are not commercially available or known in the art, e.g. agents containing both a isothiocyanate group and an isocyanate group.

The direct linkage of an alcohol-containing polysaccharide to an amine-containing protein vie reductive amination is known for linking antigenic polysaccharides to carrier proteins for the preparation of vaccines. Aldehyde groups are prepared on either the reducing end [Poren et al. (1985) *Mol. Immunol.*, 22:907–919] or the terminal end [Anderson et al. (1986) *J. Immunol.*, 137:1181–1186] of an alcohol-containing oligosaccharide or relatively small polysaccharide, which are then linked to an amine group in the protein via reductive amination. U.S. Pat. No. 4,356,170 discloses such preparation of useful polysaccharides that are reduced and then oxidized to form compounds having terminal aldehyde groups that can be reductively aminated onto free amine groups of carrier proteins such as tetanus toxoid and diphtheria toxoid with or without significant cross-linking. Several of the problems associated with the attachment of biomolecules to macromolecules are overcome by use of the reagents and processes described hereinafter.

BRIEF SUMMARY OF THE INVENTION

The present invention provides reagents and processes for the linking of alcohol-containing macromolecules, M, to amine-containing biomolecules, B. The compositions of the present invention are linking reagents, linking reagent precursors and reacted linking reagents having (i) an isothiocyanate or a thiourea derivative of an amine-containing biomolecule B, and (ii) one or two other phenyl substituents in the meta- or para-position that is (a) isocyanate, (b) acylazide, or (c) a urethane derivative of an alcohol-containing macromolecule M. Examples of alcohol-containing macromolecules, M, include but are not limited to polysaccharides and hydroxylated silica derivatives. Examples of amine-containing biomolecules, B, include but are not limited to nucleic acids and polypeptides.

A general chemical formula for a linking reagent or linking reagent precursor is shown below having (i) isothiocyanate, and (ii) one or two other phenyl substituents in the meta- or para-position that is (a) isocyanate, (b) acylazide, or (c) a urethane derivative of an alcohol-containing macromolecule M.

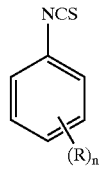

The subscript, n, is 1 or 2, denotes the number of R substituents on the phenyl ring. R is —NHC(O)—O—M, —NCO or —C(O)$N_3$., with R of —NCO or —C(O)$N_3$ in linking reagent precursors. M is a reacted alcohol-containing macromolecule. The R phenyl substituents are in the meta-, di-meta- or para-positions relative to the isothiocyanate group. The di-meta di-substituted phenylisothiocyanate is preferred over the meta, para-di-substituted phenylisothiocyanate.

A general formula for a reacted linking reagent of the present invention is shown below having (i) a thiourea derivative that is a reaction product of an amine-containing biomolecule, B, and an isothiocyanate, and (ii) one or two other phenyl substituents in the meta- or para-position that is a urethane derivative of an alcohol-containing macromolecule, M. The subscript n is 1 or 2, as before.

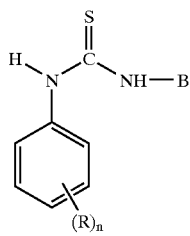

The isothiocyanate moiety of the linking reagent of the invention reacts with a primary amino group of a biomolecule B to be linked using the linking reagent, to form a thiourea moiety. In the balanced chemical reaction, there is effectively no leaving group from the reaction of the isothiocyanato group with the amino group. Thus, in some embodiments, purification issues due to reaction side products and the costs associated therewith are eliminated.

Some embodiments of linking reagent precursors are chemically facile and relatively inexpensive to prepare. Some embodiments of the linking reagent precursors are stable enough for preparation and shipment with a reasonable shelf life.

In some embodiments of the invention, linking reagents are useful for increasing the hydrodynamic volume of biomolecules, which may prolong the half-life of a biomolecule circulating in blood in a living body. In some embodiments, linking reagents are useful for linking a biomolecule to a surface.

The various embodiments of the present invention has several benefits and advantages, however all embodiments do not necessarily provide all of the below-listed benefits and advantages. Further benefits and advantages of embodiments of the invention will be recognized by workers in the art.

One benefit of several embodiments of the invention is that it provides an embodiment of a novel, activated pegylation reagent that permits rapid, efficient, one-step production of pegylated biomolecules having stable, enhanced physiological properties in a predictable and reproducible manner on a meaningful, economical scale.

An advantage of several embodiments of the invention is that it provides an embodiment of a reagent that does not suffer from a significant hydrolysis rate in aqueous reaction media that are buffered at a pH value of about 5.5 to about 8.5, maintains good rates of reactivity, is specific for primary amine groups in target biomolecules and does not produce a leaving group upon covalent attachment to the target biomolecule.

A further benefit of several embodiments of the invention is that it provides an embodiment that permits direct PEG modification of one or more-amino (preferably —$NH_2$) groups or moieties on the biomolecule without first converting those amino groups to one or more sulfhydryl (—SH) groups.

DETAILED DESCRIPTION OF THE INVENTION

The present invention provides reagents and processes for the linking of alcohol-containing macromolecules, M, to amine-containing biomolecules, B. The compositions of the present invention are linking reagents, linking reagent precursors and reacted linking reagents having (i) an isothiocyanate or a thiourea derivative of an amine-containing biomolecule B, and (ii) one or two other phenyl substituents in the meta- or para-position that is (a) isocyanate, (b) acylazide, or (c) a urethane derivative of an alcohol-containing macromolecule M. Examples of alcohol-containing macromolecules, M, include but are not limited to polysaccharides and hydroxylated silica derivatives. Examples of amine-containing biomolecules, B, include but are not limited to nucleic acids and polypeptides.

A general chemical formula for a linking reagent or linking reagent precursor is shown below having (i) isothiocyanate, and (ii) one or two other phenyl substituents in the meta- or para-position that is (a) isocyanate, (b) acylazide, or (c) a urethane derivative of an alcohol-containing macromolecule M.

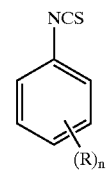

The subscript, n, is 1 or 2, denoting the number of R substituents on the phenyl ring. R is —NHC(O)—O—M, —NCO or —C(O)$N_3$. M is a reacted alcohol-containing macromolecule. The R phenyl substituents are in the meta-, di-meta- or para-positions relative to the isothiocyanate group.

A general chemical formula for a linking reagent precursor having isothiocyanate and isocyanate moieties is shown below, with n being 1 or 2, as before.

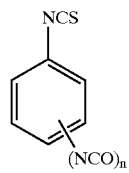

A general chemical formula for a linking reagent precursor having isothiocyanate and the precursor to the isocyanate, an acyl azide, is shown below, with n being 1 or 2, as before.

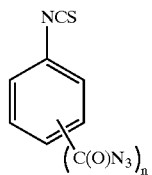

A general formula for a linking reagent that is a kind of activated alcohol-containing macromolecule is shown below, having an isothiocyanate group and —NHC(O)—O—M, where M is a reacted alcohol-containing macromolecule, with n being 1 or 2, as before. In a preferred embodiment where n is 1, the isothiocyanate moiety is in the 4-position (para) relative to the —NHC(O)—O—M.

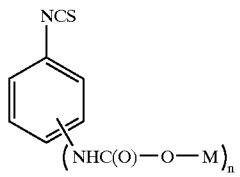

The isothiocyanate moiety of the linking reagent of the invention reacts with a primary amino group ($H_2N$—B) to form a thiourea moiety, as shown in Scheme 2 below. In the balanced chemical reaction, there is effectively no leaving group from the reaction of the thiocyanato group with the amino group. The linking reagent can also react with a secondary amine.

Scheme 2

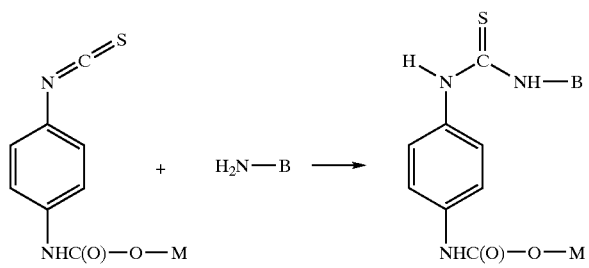

Primary amines present in a typical protein are part of a lysine (Lys or K; amino pK=10.5) amino acid residue, and also the amino terminus of the peptide backbone.

A general formula for a reacted linking reagent of the present invention is shown below having (i) a thiourea derivative that is a reaction product of an amine-containing biomolecule, B, and an isothiocyanate, and (ii) one or two other phenyl substituents in the meta- or para-position that is a urethane derivative of an alcohol-containing macromolecule, M. The subscript n is 1 or 2, as before.

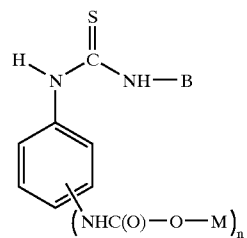

Also contemplated is an alcohol-containing macromolecule, M, that is derivatized with more than one phenylisothiocyanate group. A general formula shown below illustrates a macromolecule having two phenylisothiocyanate groups. Such a molecule is useful for crosslinking two biomolecules, B, or two amino groups within a biomolecule.

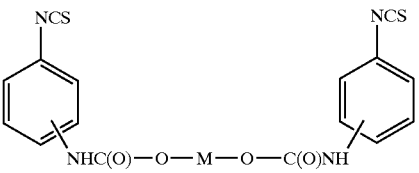

A preferred form of the reagent for a non-crosslinking pegylation reagent, represented by the formula shown below, is a phenyl isothiocyanate derivative of methoxypolyethylene glycol (mPEG).

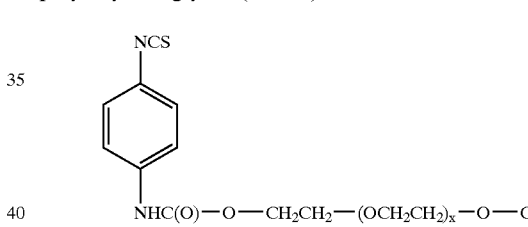

The methoxy-PEG moiety in the formula above is represented by —(O)—$CH_2CH_2$—$(OCH_2CH_2)_x$—O—$CH_3$, where x is an average repeat unit number that is about 5 and about 500, preferably about 50 to about 300.

A preferred form of the reagent for a crosslinking pegylation reagent, represented by the formula shown below, is a di-(phenylisothiocyanate) derivative of PEG.

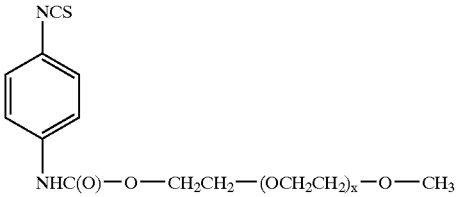

The PEG moiety in the formula above is represented by —(O)—$CH_2CH_2$—$(OCH_2CH_2)_x$—O—, where x is an average repeat unit number that is about 5 and about 500, preferably about 50 to about 300.

A preferred form of the reagent for a linking pegylation reagent where n is 2, represented by the formula shown below, is a di-meta pegylated derivative of phenylisothiocyanate.

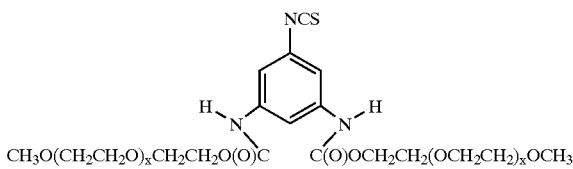

CH₃O(CH₂CH₂O)ₓCH₂CH₂O(O)C     C(O)OCH₂CH₂(OCH₂CH₂)ₓOCH₃

The mPEG moiety in the formula above is represented by —(O)—CH₂CH₂—(OCH₂CH₂)ₓ—O—CH₃, where x is an average repeat unit number that is about 5 and about 500, preferably about 50 to about 300.

The isothiocyanate moiety of the linking reagent of the invention reacts with a primary amino group of a biomolecule B to be linked using the linking reagent, to form a thiourea moiety. In the balanced chemical reaction, there is effectively no leaving group from the reaction of the isothiocyanato group with the amino group. The linking reagent can also react with a secondary amine. Preferably, for a protein, the primary amine is from the side chain of lysine or the amino terminus.

A contemplated biomolecule may be a polypeptide such as an antibody, enzyme, or protein, or a nucleic acid. Some exemplary polypeptides that benefit from pegylation include, but are not limited to, hemoglobin, bilirubin oxidase and insulin. Several contemplated biomolecules are discussed in *Polyethylene Glycol Chemistry: Biotechnical and Biomedical Applications*, J. M. Harris, ed. Plenum, NY, 1992 and *Polyethylene Glycol Chemistry and Biological Applications*, J. M. Harris and S. Zalipsky, eds., ACS, Washington, 1997. In another embodiment, the invention contemplates the linkage of the isothiocyanate to an amine of a biomolecule that is not a typical peptide residue. The invention contemplates the linking of an amine-containing biomolecule such as a drug or pro-drug, a hapten, a cytokine, a ligand for a receptor, a peptide analog, a nucleic acid base or nucleic acid analog.

In a method for providing a pegylated protein, an amine-containing protein is linked to a large, alcohol-containing PEG macromolecule, such as a PEG-phenyl isothiocyanate compound. Such a pegylated protein provides a protein that can circulate in the blood with a longer half-life than the non-pegylated protein.

In a method for providing an antibody linked to a surface, an amine-containing antibody is linked to an alcohol-containing cellulose derivatized with a phenyl isothiocyanate compound. Such a linked antibody is useful, for example in methods where separation between material that binds to the antibody from material that does not bind to the antibody is desired.

In a method for providing a protein linked to a surface, an amine-containing antibody is linked to an alcohol-containing cellulose derivatized with a phenyl isothiocyanate compound.

In a method for providing a ligand linked to a surface, an amine-containing ligand is linked to an alcohol-containing surface that has been derivatized with a phenyl isothiocyanate. Such a linked ligand is useful, for example in methods where separation between material that binds to the ligand from material that does not bind to the ligand is desired. Such an alcohol-containing surface might be a cellulose membrane or a silica bead having reactive hydroxyl groups.

In a method for providing a multi-subunit protein with enhanced stability, amine-containing proteins are crosslinked intramolecularly with a bifunctional alcohol-containing molecule, such as a PEG di-(phenylisothiocyanate) compound. Such a cross-linked multisubunit protein is useful, for example in studies of the relationships between subunits or to ascertain what proteins are in a complex, such as a transcription complex with effectors.

In an embodiment where n is 1, the R group is preferably in the para position. Thus, in a preferred embodiment where n is 1, the isothiocyanate moiety is in the 4 position (para) relative to the isocyanate (—NCO), —C(O)N₃, or —NHC(O)—O—M moiety.

In an embodiment where n is 2, there are two R substituents on the phenyl ring. The di-meta di-substituted phenylisothiocyanate is preferred over the meta, para-di-substituted phenylisothiocyanate. In an embodiment where n is 2, the invention contemplates R groups that are not identical, such as different M groups in —NHC(O)—O—M, or an —NCO group and an —NHC(O)—O—M group. Thus, reaction of less than 100 percent of the —NCO to form —NHC(O)—O—M is contemplated, as is the use of a mixture of macromolecular forms (e.g. PEG that has a range of chain lengths, as is typical in some commercially available PEG preparations).

The azido compound, where R is —C(O)N₃, is stable, and is contemplated for use as a general precursor linking reagent. When R is —NHC(O)—O—M, M is an alcohol-containing macromolecule is derivatized with one or more, but preferably only one or two, phenylisothiocyanate groups. Where M is derivatized with more than one phenylisothiocyanate group, the reagent is a crosslinking reagent. Where M is PEG, and M is derivatized with more than one phenylisothiocyanate group, the reagent is a crosslinking pegylation reagent.

The invention contemplates the linkage of the isothiocyanate group to an amine, preferably a primary amino group of a biomolecule B to be linked using the linking reagent. Such a biomolecule is preferably a nucleic acid or a polypeptide, e.g. an antibody, enzyme, or protein.

In an embodiment, the invention contemplates the linkage of the isothiocyanate to an amine of a biomolecule that is not a typical peptide residue. The invention contemplates the linking of an amine-containing biomolecule such as a drug or pro-drug, a cytokine, a ligand for a receptor (e.g. example streptavidin), a peptide analog, a nucleic acid base or nucleic acid analog.

In a method for providing a pegylated polypeptide, an amine-containing polypeptide is linked to a large, alcohol-containing PEG macromolecule, such as a PEG-phenyl isothiocyanate compound. Such a pegylated polypeptide provides a polypeptide that can circulate in the blood with a longer half-life than the non-pegylated form. Such a pegylated polypeptide is thus useful in a method of treating a mammal (including homo sapiens) involving the administration of a polypeptide.

The invention contemplates a method of making a stabilized peptide through attachment of a polyethylene glycol to a peptide. In a preferred embodiment, a bifunctional molecule (a phenyl group with an isothiocyanate moiety and an isocyanate moiety) serves to crosslink the polyethylene glycol moiety to a peptide via an amine group, preferably a primary amino group, such as on a lysine side chain.

A polyethylene glycol (PEG) compound can itself be quite varied in composition, but contains at least one poly (oxyethylene) chain [(—CH₂CH₂O—)ₓ] having an average molecular weight of about 300 (x is 5) to about 22,000 (x is 500), with an average molecular weight of about 2,300 (x is 50) to about 13,300 (x is 300) being more preferred. More specifically, the reacted PEG compound group M of the linker corresponds to the formula —CH₂CH₂—(CH₂CH₂O)ₙ—CH₂CH₂Y where X, n and R are defined and discussed hereinbelow.

In the above formula, x is a number having an average value of about 5 to about 500, and more preferably about 50 to about 300. It is well known that the higher molecular weight PEG compounds are usually mixtures rather than pure compounds having a single molecular weight. As a result, x, the number of ethyleneoxy repeating units, is a number that is an average number. The terminal Y group is —OH or a $C_1$–$C_{10}$ hydrocarbyl ether (alkoxy group) having a molecular weight of up to about one-tenth of the —$(CH_2CH_2O)_n$— portion.

Exemplary $C_1$–$C_{10}$ hydrocarbyl ether groups are well known and include alkyl, alkenyl, alkynyl and aromatic ethers. Illustrative $C_1$–$C_{10}$ ethers thus include methyl, which is most preferred, ethyl, isopropyl, n-butyl, cyclopentyl, octyl, decyl, 2-cyclohexenyl, 3-propenyl, phenyl, 1-naphthyl, 2-naphthyl, benzyl, phenethyl and the like ethers. These ether groups can also be named methoxy, ethoxy, isopropoxy, n-butoxy, cyclopentyloxy, octyloxy, decyloxy, 2-cyclohexenyloxy, 3-propenyloxy, phenoxy, 1-naphthoxy, 2-naphthoxy, enzyloxy and phenethyloxy. A $C_1$–$C_6$ hydrocarbyl group is a particularly preferred Y group.

The molecular weight of a $C_1$–$C_{10}$ hydrocarbyl ether can be up to about one-tenth of the weight of the —$(CH_2CH_2O)_x$— portion of the PEG group. Thus, where x is 20, the —$(CH_2CH_2O)_x$— portion has a molecular weight of 880 (20×44) so that the molecular weight of Y can be up to about 90, or about the weight of a phenoxy group. It is more preferred that the molecular weight of the $C_1$–$C_{10}$ hydrocarbyl group be about 0.2 to about 2 percent of the molecular weight of the —$(CH_2CH_2O)_x$— portion.

The linker molecules of the invention are useful in a variety of methods and assays involving amine-containing peptides or proteins. The invention can be used so that detection enzymes are the amine-containing biomolecule B that is linked to a macromolecule or surface, M, such as cellulose, for use in an assay. Skilled workers in the art can appreciate other methods of using the linker of the invention in their assays with their own amine-containing biomolecules, B, and alchohol-containing macromolecules, M.

For example, streptavidin, such as the wild type or mutants taught in U.S. Pat. No. 6,312,916 granted Nov. 6, 2001, can be useful in binding biotinylated molecules. The streptavidin is linked to a macromolecule, such as PEG, which can change a molecular weight cut off and permit dialysis-type binding assays. The streptavidin B is linked to a macromolecule such as a cellulose membrane, M, which can then be washed with solutions that may contain biotinylated molecules.

Contemplated hydroxy-containing surfaces include, but are not limited to, appropriately derivatized silica, cellulose or gold.

Contemplated hydroxy-containing macromolecules include polysaccharides. On large polysaccharides, one or more of the hydroxy groups may be reacted with a linking reagent precursor. Reaction with a di-meta compound may result in crosslinking of a polysaccharide chain. The carbohydrate itself can be synthesized by methods known in the art, for example by enzymatic glycoprotein synthesis as described by Witte et. al. (1997) *J. Am. Chem. Soc.*, 119:2114–2118.

Several oligosaccharides, synthetic and semi-synthetic, and natural, are discussed in the following paragraphs as examples of oligosaccharides that are contemplated haptens to be used in making a HBc conjugate of the present invention. U.S. Pat. No. 4,220,717 also discloses a polyribosyl ribitol phosphate (PRP) hapten for *Haemophilus influenzae* type b. Andersson et al., EP-0 126 043-A1, disclose saccharides that can be used in the treatment, prophylaxis or diagnosis of bacterial infections caused by *Streptococci pneumoniae*. European Patent No. 0 157 899-B1, the disclosures of which are incorporated herein by reference, discloses the isolation of antigenic pneumococcal polysaccharides.

The optimal ratio of macromolecule polysaccharide M to biomolecule B in the linked form depend on the particular polysaccharide, the biomolecule, and the linker molecule used.

In a method for providing an antibody linked to a surface, an amine-containing antibody is linked to an alcohol-containing cellulose derivatized with a phenyl isothiocyanate compound or other hydroxy-containing surface. Such a linked antibody is useful, for example in methods where separation between material that binds to the antibody from material that does not bind to the antibody is desired.

In a method for providing a protein linked to a surface, an amine-containing antibody is linked to an alcohol-containing cellulose derivatized with a phenyl isothiocyanate compound.

In a method for providing a ligand linked to a surface, an amine-containing ligand is linked to an alcohol-containing cellulose derivatized with a phenyl isothiocyanate. Such a linked ligand is useful, for example in methods where separation between material that binds to the ligand from material that does not bind to the ligand is desired.

In a method for providing a multi-subunit protein with enhanced stability, amine-containing proteins are crosslinked intramolecularly with a bifunctional alcohol-containing molecule, such as a PEG di-(phenylisothiocyanate) compound. Such a cross-linked multisubunit protein is useful, for example in studies of the relationships between subunits or to ascertain what proteins are in a complex, such as a transcription complex with effectors. Also contemplated is linking between different molecules in an associated complex, for example transcription factors with RNA polymerase.

A preferred pegylation reagent according to the invention is made using methods known in the art or their equivalents.

In one example of the invention, the preparation of a PEG molecule having a phenyl isothiocyanate activating group is carried out as shown in Scheme 3, below. Briefly, a para-aminobenzoic acid is reacted with thiophosgene to produce 4-carboxyphenyl isothiocyanate, as described in Example 1. The carboxy moiety is activated as the azide to form isothiocyano benzoyl azide by known methods, such as that described in Example 2. The azide-activated carboxy moiety was then heated to cause internal rearrangement to isocyanophenyl isothiocyanate, by the Curtius Rearrangement described in Example 3.

Scheme 3

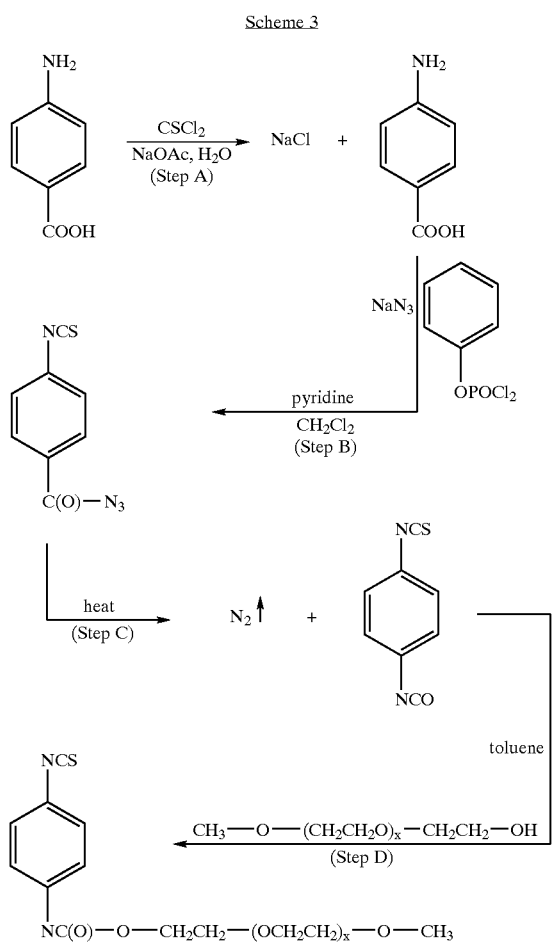

The invention contemplates linking reagents having one equivalent of hydroxy-containing macromolecule. A contemplated linking reagent is not limited to a para-substituted phenyl isothiocyanate. Meta- and di-meta-substituted phenyl isothiocyanate compounds are also contemplated. The synthesis of the para-substituted compound is shown below in Examples 1–3, starting with para-aminobenzoic acid. A corresponding meta-substituted aminobenzoic acid compounds are commercially available.

The invention contemplates bifunctional linking reagents having more than one phenyl isothiocyanate groups, which are useful as crosslinking reagents. Using the azide-activated synthetic isocyanate reaction described above, a hydroxy-containing macromolecule is linked to the phenyl isothiocyanate group. The use of a macromolecule with more than one hydroxy group, and appropriate adjustments of stoichiometry and reaction conditions, results in a reagent that has more than one phenyl isothiocyanate group. For example, a bifunctional PEG reagent is made using a PEG diol, as illustrated by Example 4, below. Such bifunctional linking reagents are useful for linking two amine-containing biomolecules (the same or different biomolecules).

The invention contemplates linking reagents having one or more hydroxy-containing macromolecules on a single phenyl isothiocyanate group. Such reagents are made using the analogous procedures to those described herein in detail for the mono-substituted phenyl isothiocyanate compound. For example, a di-meta reagent is made starting with 5-aminoisophthalic acid, commercially available (e.g. Aldrich Product No. 18,627-9). The conversion of the amino group to isothiocyanate then proceeds as described in the Examples below, using CSCl$_2$, NaOAc and H$_2$O, using methods known in the art. A preferred method of making a di-meta reagent is shown in Scheme 4 below. Commercially available amino isophthalic acid serves as the starting material that is converted to the corresponding isothiocyanate compound, 3,5-dicarboxyphenyl isothiocyanate, using thiophosgene, C(S)Cl$_2$, in the presence of an aqueous solution of sodium acetate as illustrated below in Example 5. The two carboxylic acid moieties are then activated with sodium azide in the presence of phenyl dichlorophosphate and pyridine, as illustrated in Example 6 below, to provide the corresponding acylazido phenylisothiocyanate. The acylazido moieties convert smoothly to isocyanate moieties via the Curtius rearrangement, which then react with an alcohol-containing macromolecule, such as PEG, to provide a contemplated di-meta-substituted phenylisothiocyanato reagent.

Scheme 4

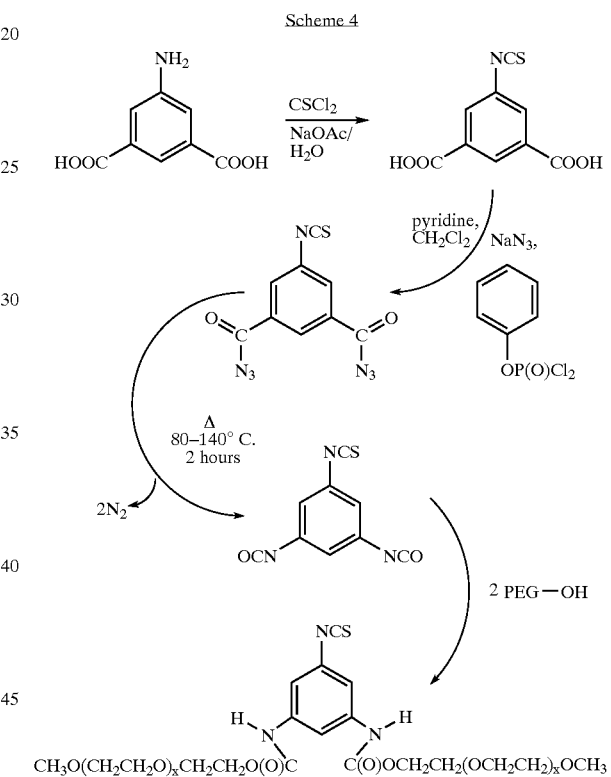

The linking of two hydroxy-containing macromolecules to the di-meta-substituted reagent also proceeds by methods known in art, examples of which are provided hereinbelow. Preferably, one hydroxy group from each of two macromolecules reacts with a single di-meta isocyanate-substituted phenyl isothiocyanate compound to form a di-meta linking reagent.

Thus is it recognized that the methods described herein are useful to activate a variety of hydroxy-containing macromolecules, including hydroxy and polyhydroxy compounds. Contemplated examples include but not limited to methoxy PEG, PEG-diols and branched PEGs of various molecular weights. Hydroxy and polyhydroxy compounds other that polyethylene glycols are contemplated, including but not limited to celluloses and starches. Such reagents adapting methods known in the art for reacting phenylisocyanates with hydroxl-containing molecules, such as described herein adapted for the molecules of interest, by adjusting the amount of p-isothiocyanobenzoylazide added to match the correct stoichiometry of macromolecular hydroxyls present. Normally, a stoichiometric or slight excess (zero to ten percent molar excess relative to the hydroxy; where zero percent excess is a one-to-one molar ratio) of the azide is added. For instance, dry, insoluble surfaces, i.e., cellulose bearing a plurality of primary hydroxyl groups is activated by soaking the surface in a solution of p-isothiocyanophenyl isocyanate at 20–60° C. (prepared in situ), as described in Example 5, below, or hydroxy-derivatized silica. The activated surface is ready for linking to an amine-containing molecule, useful for a wide variety of applications.

The activated supports thus obtained are useful for immobilizing functional proteins such as enzymes or antibodies under mild conditions (e.g. pH 7.4–8.25 10 mm bicarbonate buffer). Likewise, immunoconjugates of small, hydroxy-containing haptens, e.g. vitamin B-12, hydroxyprogesterone, and digoxigenin, are made utilizing a contemplated isothiocyanophenyl isocyanate. A protocol for linking small, hydroxy-containing molecules to an isocyanate compound is described in M. E. Annunziato, et al., *Bioconjugate Chem.*, 4:212–218 (1993), the disclosures of which are incorporated in full herein by reference.

The phenyl isothiocyanate moiety is stable against hydrolysis in aqueous buffers, and it maintains excellent rates of reaction specifically with primary amines in target biomolecules. Bi- and multi-functional linking reagents are thus possible and practical for the efficient derivatization of target molecules for the purpose of establishing inter and/or intra molecular crosslinks which stabilize native tertiary structure.

EXAMPLE 1

Synthesis of 4-carboxyphenyl Isothiocyanate

Para-aminobenzoic acid (0.2 moles; 26 grams of 99 percent pure from Aldrich Chemical, Milwaukee, Wisconsin) was dissolved in acetone (400 mL) at room temperature (about 20 degrees Celsius). Activated carbon (about 5 grams; Darco® G60) was added, and the mixture was stirred (magnetic stir bar) for 5 to 10 minutes. The entire solution was filtered, yielding a much lighter-colored solution of p-aminobenzoic acid than was initially formed.

Sodium acetate (0.3 moles, 25 grams; dissolved in about 200 mL of deionized water) was added to the filtrate, now contained in a 4 liter vacuum flask. A vacuum was applied to the flask with an intermediate dry ice/acetone trap between the 4 liter flask and the vacuum pump. Reduced pressure was maintained until much of the original acetone had evaporated off of the p-aminobenzoic acid solution (down to about 300 mL volume). The flask was chilled to between about zero and five degrees Celsius.

Thiophosgene (about 40 grams of neat red liquid) were added in one portion to the cooled, acetone-stripped slurry of p-aminobenzoic acid, while stirring rapidly with an overhead paddle stirrer. A tan precipitate formed almost immediately upon addition of the thiophosgene, along with considerable foaming. After the foaming subsided (about 10 minutes), the insoluble precipitate was filtered and dried in vacuo until it was a free-flowing powder.

The crude product was re-crystallized from hot (about 80° C.) glacial acetic acid to yield light yellow needles of 4-carboxyphenyl isothiocyanate (about 16 grams) after drying in vacuo. Considerable product remained in the mother liquor, which was not recovered.

Elemental analysis of the yellow crystals yielded: Carbon (found 53.38 percent, theory 53.63 percent); hydrogen (found 2.76 percent, theory 2.79 percent); nitrogen (found 7.58 percent, theory 7.82 percent). The crystals darkened but did not melt at 220° C. The infrared spectrum of the crystals was consistent with that expected for 4-carboxyphenyl isothiocyanate.

EXAMPLE 2

Synthesis of 4-isothiocyanobenzoyl Azide

A portion of the 4-carboxyphenyl isothiocyanate (15 grams) from Example 1 was suspended in dry methylene chloride (200 mL) in a 1 liter side-arm vacuum flask, along with pyridine (16 grams; 0.2 M), phenyl dichlorophosphate (Aldrich Cat. No. P.2, 238-9; 0.1 M) and sodium azide (6.5 grams; 0.1 M). The mixture was stirred overnight (about 15 hours) at room temperature. The stirred mixture was then washed in a separatory funnel with water (200 mL) and then sulfuric acid (200 mL of 0.1 N $H_2SO_4$). The acid-washed methylene chloride layer was dried with anhydrous magnesium sulfate ($MgSO_4$).

The dried methylene chloride reaction solution was evaporated under vacuum in a rotary evaporator at room temperature or lower (less than or equal to about 20° C.). The resulting light tan crystals were dissolved in a minimum of ethyl ether at room temperature. The re-crystallization solution was treated with activated carbon (Darco® G60) and filtered. The resulting light-colored solution was evaporated to dryness in vacuo at a temperature not exceeding 20° C. Nearly white crystals were obtained melting at 68–72° with evolution of nitrogen, consistent with azide decomposition.

The elemental analysis of the 4-isothiocyanobenzoyl azide crystals gave the following results: Carbon (found 46.85 percent, theory 47.05); Hydrogen (found 2.09 percent; theory 1.96 percent); Nitrogen (found 26.87 percent; theory 27.45 percent). The infrared spectrum of the crystals (FTIR) conformed to 4-isothiocyanobenzoyl azide (e.g. strong, broad band from about 2000 to about 2200 $cm^{-1}$ is from N=C=O and N=C=S stretching modes; and a strong absorption due to azide at about 980–1000 $cm^{-1}$) The compound is stable at room temperature but was stored in the freezer.

EXAMPLE 3

Synthesis of 4-isothiocyanophenyl Isocyanate and PEG Reagent

The nearly white 4-isothiocyanobenzoyl azide from Example 2 was thermally decomposed at about 75°–104° C. (Curtius Rearrangement) smoothly and quantitatively as a solution in dry refluxing toluene. The resulting 4-isothiocyanophenyl isocyanate (also known as 4-isocyanophenyl isothiocyanate, shown below) product is represented by the following chemical formula. The 4-isocyanophenyl isothiocyanate was not isolated, but reacted as formed in situ with the hydroxyl-containing PEG according to the following description. An infrared spectrum of the composition containing 4-isocyanophenyl isothiocyanate showed the decrease in the azide band at about 980–1000 $cm^{-1}$ along with increased complexity of the absorbance in the N=C=O and N=C=S region of the spectrum from about 2000 to about 2300 $cm^{-1}$.

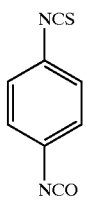

A 2-liter, 3-necked flask was equipped with a thermometer, overhead stirrer with motorized drive, heating mantle with rheostat, short column with Dean-Stark trap and condenser. The flask contained toluene solvent (500 mL) charged with methoxypolyethylene glycol having a low diol content ("PEG methyl ester", MW 5000; 50 grams; 10 mL; manufactured by NOF Corp. Japan, available as catalog No. 2M000H01 from Shearwater Corp., Huntsville, Ala.; HO—$CH_2CH_2$—($OCH_2CH_2$)$_x$—O—$CH_3$, where x is about 112).

The PEG methyl ether (mPEG) mixture was stirred and heated to reflux (about 104° C.) and any water present was azeotropically removed as it accumulated in the Dean-Stark trap. When no additional water formed in the Dean-Stark trap, heating was discontinued and the reaction vessel and its contents were cooled under a dry $N_2$ blanket until the internal reaction solution temperature was less than about 60° C.

After the reaction solution temperature fell to less than about 60° C., p-isothiocyanobenzoyl azide (0.5 grams from Example 2) was added to the reaction as a solid (through thermometer port), and heating was resumed. A brisk and steady stream of nitrogen exited the reactor during the initial about 15 to about 30 minutes after heating was resumed. Heating was continued (reflux) for an additional hour after nitrogen evolution ceased, as monitored by bubble trap at the exit of condenser. Heating was then discontinued and the flask and contents allowed to cool to room temperature overnight (about 16 hours), providing mPEG-O—p-carbamoylphenyl isothiocyanate.

Workup and purification of phenylisothiocyanate-activated mPEG of this example was accomplished by concentrating the reaction solution under vacuum by means of a rotary evaporator. The remaining viscous oil was triturated with anhydrous ethyl ether to induce crystallization of the activated mPEG (nearly white). The ether trituration induces crystallization and extracts excess, unreacted p-isothiocyanophenyl isocyanate.

The crude product was filtered and dried in vacuo (yield 51 grams). The dried crude product was dissolved and stirred with water (500 mL deionized). A slight amount of water-insoluble matter was filtered out of the phenylisbthiocyanate-activated mPEG using 0.2$\mu$ glass mat filter paper, yielding a clarified filtrate. The clarified filtrate was extracted with methylene chloride (2×200 mL) in a separatory funnel. The methylene chloride extract was dried with anhydrous magnesium sulfate, and filtered. The dried, filtered extract was concentrated under vacuum (rotary evaporator) to a viscous oil. Product was precipitated by addition of diethyl ether. The recrystallized phenylisothiocyanate-activated mPEG product was filtered and dried under vacuum to yield a white solid (48 grams). Elemental analysis of the phenylisothiocyanate-activated mPEG: Carbon (found 54.09 percent, theory 54.5 percent); Hydrogen (found 8.95 percent; theory 9.09 percent); Nitrogen (found 0.32 percent, theory 0.5 percent).

EXAMPLE 4

Synthesis of Bifunctional PEG Reagent 4-isothiocyanobenzoyl azide is decomposed and reacted in situ with the two alcohol moieties of a PEG diol compound to form a PEG isothiocyanate crosslinking reagent. A 2-liter, 3-neck flask is equipped with a thermometer, overhead stirrer with motorized drive, heating mantle with rheostat, short column with Dean-Stark trap and condenser. The flask contains toluene solvent (500 mL) charged with polyethylene glycol ("PEG diol", MW 5000; 25 grams, HO—$CH_2CH_2$—($OCH_2CH_2$)$_x$—O—H, where x is about 112).

The PEG diol/toluene mixture is stirred and heated to reflux (~104° C.) and any water present is azeotropically removed as it accumulates in the Dean-Stark trap. When no additional water forms in the Dean-Stark trap, heating is discontinued and the reaction vessel and its contents are cooled under a dry $N_2$ blanket until the internal reaction solution temperature is less than about 60° C.

After the reaction solution temperature falls to less than about 60° C., p-isothiocyanobenzoyl azide (0.5 grams from Example 2) is added to the reaction, and heating is resumed. Nitrogen evolution is monitored. Heating is continued at reflux for an additional hour after the nitrogen evolution ceases. Heating is then discontinued and the flask and contents cooled, providing the PEG isothiocyanate crosslinking reagent shown below.

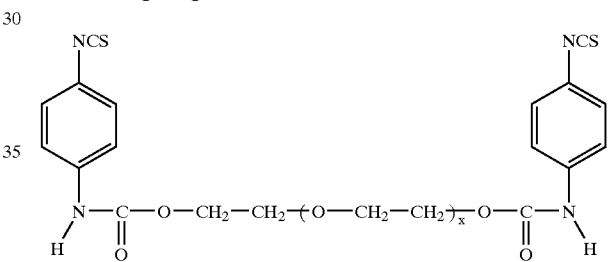

The PEG crosslinking reagent product is dried down, triturated with ether and crystallized. The PEG crosslinking reagent is dissolved in water, extracted into methylene chloride, dried and re-crystallized.

EXAMPLE 5

Preparation of 3,5-dicarboxyphenyl Isothiocyanate

Acetone (1.4 L), sodium acetate in water (1.0 L of 1 M) and 5-aminoisophthalic acid (50 g; Aldrich Catalog No. 18,627-9) were added to a flask (4 L) equipped with a stirrer. The pH of the resulting slurry was adjusted to 6.8–7.0 by dropwise addition of a 50 percent sodium hydroxide aqueous solution. An additional 500 mL of water yielded a homogeneous, yellow solution of 5-aminoisophthalic acid which was treated with activated carbon, filtered and chilled to 5–10° C. by the addition of ice cubes.

To the rapidly stirred and chilled solution was then added 25.0 mL of thiophosgene liquid (Aldrich Catalog No. 1,515-0) in one shot. After stirring for 30 minutes, concentrated hydrochloric acid was added dropwise until the pH of the resulting reaction was 3–4, causing the crude product to precipitate.

Two recrystallizations from a minimum of 85° C. acetic acid yielded pale yellow crystals of 3,5-dicarboxyphenyl isothiocyanate. Elemental and IR analyses conform to the expected results. Elemental analysis of the 3,5-dicarboxyphenylisothiocyanate: Carbon (found 46.34 percent, theory 48.43 percent); Hydrogen (found 3.16 percent; theory 2.24 percent); Nitrogen (found 4.89 percent, theory 6.27 percent).

EXAMPLE 6

Preparation of 3,5-di-Acylazidophenyl Isothiocyanate

The di-carboxylic acid compound from the preceding Example, 3,5-dicarboxyphenyl isothiocyanate (8.9 g, 0.04 moles), was reacted with pyridine (16 g; 0.2 moles) and phenyl dichlorophosphate (226 M; 0.1 moles) and sodium azide (6.56 g; 0.1 moles) in methylene chloride (300 mL) in the manner described in Example 2, above. Recrystallization from methylene chloride produced cream-colored, crystalline powder of the di-acylazidophenyl isothiocyanate (6 g; melting point 92–94° C. with evolution of nitrogen). The infrared and elemental analyses conformed to the expected results. A strong azido absorbance at about 1192 cm$^{-1}$ was observed. Elemental analysis of the 3,5-di-acylazidophenyl isothiocyanate: Carbon (found 39.99 percent, theory 39.56 percent); Hydrogen (found 1.42 percent; theory 1.09 percent); Nitrogen (found 32.21 percent, theory 35.89 percent).

EXAMPLE 7

Preparation of 3,5-di-Carbamoyl Methoxy Polyethylene Glycol

The 3,5-di-acylazido phenylisothiocyanate from Example 6 (1.26 g; about 0.005 moles) was thermally decomposed at about 92°–94° C. (Curtius Rearrangement) in dry refluxing toluene in a three-necked flask (2 L) equipped with a mechanical stirrer, a Dean-Stark trap and a condenser. The resulting 3,5-di-isocyanophenyl isothiocyanate product was not isolated, but reacted as formed in situ with methoxy polyethylene glycol (50 g; 0.01 moles) that had been prepared as described in Example 2, above. The reaction solution was heated with evolution of nitrogen and then refluxed for an additional hour after nitrogen evolution ceased.

After cooling, solvent was removed and the product crystallized from the viscous oil by trituration with anhydrous ether. The solid product was further purified by extracting the solid from an aqueous solution into methylene chloride (dried with anhydrous magnesium sulfate) reconcentrated and triturated with anhydrous ether. The purified 3,5-(di-carbamoyl mPEG) phenyl isothiocyanate (48.3 g) was nearly white.

EXAMPLE 8

Synthesis of a Cellulose Reagent

An insoluble reagent for linking amine groups of target molecules, such as proteins, is prepared from cellulose. The activated cellulose linking reagent is stored as a dry reagent with a relatively long shelf life.

Cellulose has a plurality of primary hydroxy groups. Cellulose is soaked overnight at 20–60° C. in a solution of p-isothiocyanophenyl isocyanate prepared in situ as described above in Example 3. The activated cellulose surface is washed repeatedly with fresh toluene and dried.

EXAMPLE 9

Pegylation of Hemoglobin

A para-(methoxy polyethylene glycol 5000 carbamic acid) derivative of phenyl isothiocyanate (mPEG reagent) was prepared using the methods described in Examples 1–3. Hemoglobin was purified from human red blood cells through methods known in the art. The accessible hemoglobin α-amino group was reacted with the m-PEG reagent permitting an mPEG reagent solution (1 mM) in pH 7.4 phosphate buffered saline containing hemoglobin (0.5 mM) to remain overnight (about sixteen hours) in a cold room (about 4° C.).

The reaction product was dialyzed against 10 mM potassium phosphate, pH 6.5, and subjected to purification on a CM-cellulose column. Analysis of the resulting pegylated hemoglobin by methods described in Belur N. Manjula, et al., *J. Biol. Chem.*, 275(8):5527–5534 (2000) reveal a molecular radius of 5.2 consistent with a hemoglobin modified with four molecules of methoxy PEG 5000 per hemoglobin tetramer.

The pegylated hemoglobin obtained had a slightly higher oxygen affinity as compared to unmodified hemoglobin. Thus the molecular radius measurements are consistent with the modification of the four alpha amino groups of the hemoglobin tetramer.

The disclosures of each of the patents and articles cited herein is incorporated by reference. The use of the article "a" or "an" in a claim hereinbelow is intended to include one or more, unless otherwise specifically stated.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed is:

1. The compound represented by the formula

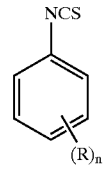

where n=1 or 2;

R is —NHC(O)—O—M;

M is A reacted alcohol-containing macromolecule; and

R is in a para-, meta- or di-meta position relative to —NCS.

2. The compound according to claim 1, wherein M is a reacted polyethylene glycol or polysaccharide.

3. The compound according to claim 2 wherein the polysaccharide is dextran, cellulose, starch or agarose.

4. The compound according to claim 1 represented by the formula

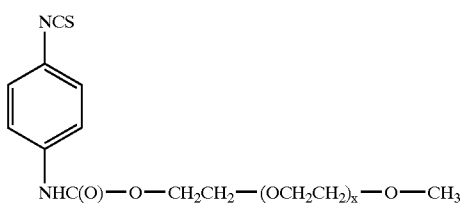

wherein M is the reacted methoxy polyethylene glycol —CH$_2$CH$_2$—(OCH$_2$CH$_2$)$_x$—O—CH$_3$; and x is an average value that is about 5 to about 500.

5. The compound according to claim 1,

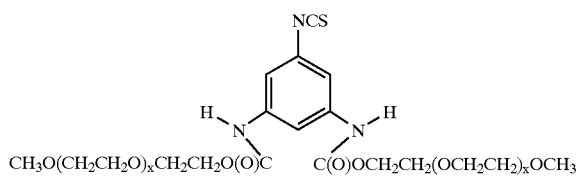

wherein said compound is represented by the formula above and x is an average value that is about 5 to about 500.

6. The compound represented by the formula

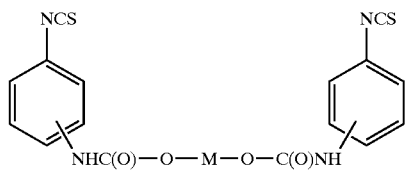

where M is a reacted alcohol-containing macromolecule.

7. The compound according to claim 6 where M is polyethylene glycol.

8. The compound according to claim 7 represented by the chemical formula

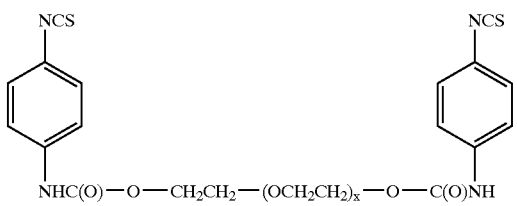

wherein x is an average value that is about 5 to about 500.

* * * * *